United States Patent [19]

Schneider et al.

[11] Patent Number: 5,322,518
[45] Date of Patent: Jun. 21, 1994

[54] VALVE DEVICE FOR A CATHETER

[75] Inventors: Stefan Schneider, Kiel; Hans O. Maier, Lohfelden, both of Fed. Rep. of Germany

[73] Assignee: B. Braun Melsungen AG, Melsungen, Fed. Rep. of Germany

[21] Appl. No.: 874,112

[22] Filed: Apr. 24, 1992

[30] Foreign Application Priority Data

Apr. 27, 1991 [DE] Fed. Rep. of Germany ... 9105229[U]

[51] Int. Cl.⁵ ...................... A61M 5/00; A61M 5/178
[52] U.S. Cl. ..................................... 604/247; 604/167
[58] Field of Search ................ 604/167, 169, 246–249, 604/256, 283, 905

[56] References Cited

U.S. PATENT DOCUMENTS

| | | | |
|---|---|---|---|
| 4,256,106 | 3/1981 | Shoor | 604/905 X |
| 4,387,879 | 6/1983 | Tauschinski | |
| 4,433,973 | 2/1984 | Kurtz et al. | 604/403 |
| 4,496,348 | 1/1985 | Genese et al. | 604/167 |
| 4,511,359 | 4/1985 | Vaillancourt | 604/411 |
| 4,610,469 | 9/1986 | Wolff-Mooij | 285/260 |
| 4,655,762 | 4/1987 | Rogers | 604/403 |
| 4,857,062 | 8/1989 | Russell | 604/256 |
| 4,878,900 | 11/1989 | Sundt | 604/119 |
| 4,998,927 | 3/1991 | Vaillancourt | 604/283 |
| 5,009,391 | 4/1991 | Steigerwald | 251/149.1 |
| 5,108,380 | 4/1992 | Herlitze et al. | 604/283 |

FOREIGN PATENT DOCUMENTS

| | | | |
|---|---|---|---|
| 3042229 | 5/1982 | Fed. Rep. of Germany . | |
| 3737665 | 5/1989 | Fed. Rep. of Germany ... | 604/905 X |
| 0674944 | 8/1990 | Switzerland ................. | 604/905 X |
| 1193759 | 6/1970 | United Kingdom .......... | 604/283 |

Primary Examiner—John D. Yasko
Assistant Examiner—Adam J. Cermak
Attorney, Agent, or Firm—Spensley Horn Jubas & Lubitz

[57] ABSTRACT

A valve device for a catheter with a catheter hub. A tubular housing has one end provided with an outer cone for fitting into an inner cone of the catheter hub and has a valve body within acting as a locking member of an axial channel for the passage of an elongate object. The housing is provided with an axially directed protrusion forming a radial space together with the outer surface of the outer cone and has a locking member cooperating with a complementary member at the catheter hub projecting into the space so as to act as a disconnection lock. Thus, a valve device is provided that is suitable for use with a catheter system destined for venous applications according to the Seldinger method, and which ensures a reliable sealing of the extracorporal end of the catheter.

9 Claims, 3 Drawing Sheets

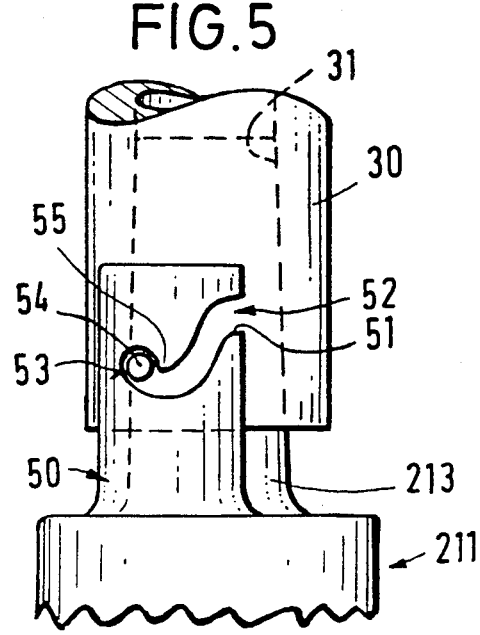
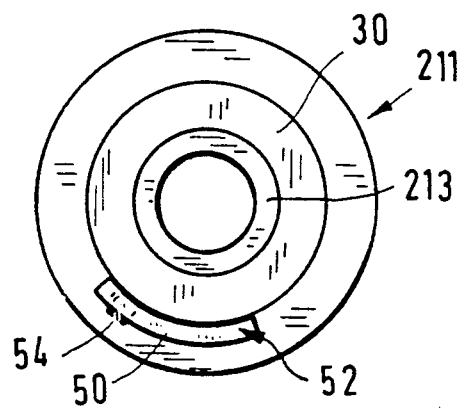

VALVE DEVICE FOR A CATHETER

BACKGROUND OF THE INVENTION

1. Field of the Invention

The invention relates to a valve device for a catheter with a catheter hub.

2. Description of Related Art

A valve device of the type mentioned before and known from German Patent 30 42 229 C2 serves to introduce elongate objects into a blood vessel through a cannula, and its outer cone is clampingly plugged into the inner cone of the hub. In this case, the valve body consists of a sequence of slotted seal elements, the sealing lips of which abut the elongate objects or each other and close the passages. This valve device can only be used as a sluice for guide wires or the like introduced into the blood vessel from outside. However, it is not suitable for a catheter system for venous applications according to the Seldinger method, wherein the catheter is threaded by its tip over a placed guide wire. This is due to the fact that the frictional forces occurring between the valve body and the guide wire strongly influence the feeling for the placement of the catheter so that the feeling for the placement is lost to a certain extent. Further, it is practically impossible in this valve device to hit the slot of the seal elements with the tip of the guide wire when threading the catheter thereon. Moreover, this known valve device is not suitable for an absolutely secure sealing closure of the passage of a catheter after the removal of the guide wire from its lumen, because the plug connection between the outer cone and the inner cone of the catheter hub is not reliably firm. There is a risk that, in the case of a longer use of a catheter, the plug conection will loosen with the movements of a patient, resulting in air possibly entering the catheter, which may be fatal to the patient if the catheter is placed in a hollow vein. In less dangerous applications, the loosening of the plug connection will cause a leak from which returning body fluid may emerge, leaking from the loosened connection and causing a contamination of the surroundings that might be hazardous to the patient and the personnel.

In another known valve device according to U.S. Pat. No. 4,387,879, similar conditions are encountered that exclude the same from utilisation in a catheter system for venous implementation according to the Seldinger method. A body adapted for limited axial displacement is disposed in a flow channel of a tubular housing, the body cooperating with a disc of elastomeric material shutting off the passage and having an axial slot. The body is designed as a sleeve with a frustoconically tapered end. It is displaced when a connection cone is applied. In doing so, the frustoconical end penetrates the slot in the disc, spreads the same and keeps it open. Thereby, friction between the slots and an elongate element inserted from outside is reduced. To take advantage thereof when threading a venous catheter equipped with this valve device onto the end of a placed guide wire, the body would have to be displaced towards the opening of the slot by means of a connection cone, which cone would in turn impede the placement of the catheter. At one end, the housing of this valve device is provided with an inner cone for the connection cone used to operate the body, and the other end of the housing has a conically tapered stud with continuous ribs that serves to hold a hubless hose pushed thereon and leading to the vessel system. Such a connection between the hose and the valve device is not reliable. Were the valve device to be placed in a conduit system, the connection might become disengaged due to movements and media flowing from or into leaks could cause hazards to the patient and/or the personnel.

It is an object of the invention to provide a valve device that is suitable for use with a catheter system destined for venous applications according to the Seldinger method, and which ensures a reliable sealing of the extracorporal end of the catheter.

SUMMARY OF THE INVENTION

According to the invention, this and other objectives are solved by providing the housing with an axially directed protrusion forming a radial space with the outer surface of the outer cone, and which has a locking element that cooperates with a complementary element at the catheter hub extending into the space, so as to form an axial disconnection lock.

The invention profits from the fact that the feeling for the reliability of the placement of a catheter according to the Seldinger method is more important than the fact that a little blood flows when the catheter is placed by being set onto the guide wire, because, in this method of placement, a blood contact cannot be avoided, anyway.

The valve device according to the present invention is only posteriorly connected to a catheter inserted into a vein by being pushed onto a placed guide wire so that, according to the Seldinger method, the catheter is placed without the valve device, but with the "feeling" being completely preserved. Only after the successfull placement of the catheter and the withdrawal of the guide wire from the catheter, will the valve device be mounted to the catheter hub in a manner not disconnectable so that the reflux of liquid and the intrusion of air are prevented. The valve device is provided separately in a catheter set with a guide wire and is set by the user after the placement of the catheter such that the device cannot be removed therefrom. The valve housing that may be permanently coupled to a catheter hub in a simple manner is locked with the catheter hub so that it cannot become detached from the catheter hub by movements of the patient. The extracorporal end of the catheter is always reliably connected with the valve device so that contaminations of the surroundings by outflowing body fluids and a hazard to the patient in the form of air entering the catheter are avoided. The safety of a catheterised mobile patient connected to a transfer system is increased by the valve device of the present invention. Further, in connection with a replacement of a catheter placed in a vessel, the valve device allows to put a guide wire through the valve device from outside over which the catheter to be removed is drawn from the vessel. The placement of the new catheter without valve may be done in the usual manner over the guide wire. When the catheter has reached the desired position, the non-disconnectable valve device of the present invention is again mounted.

Advantageously, the second end of the housing is provided with a connection profile for a connector. Preferably, the connection profile is conform to a Luer lock and allows for the connection of a continuing conduit or an operating member for the valve body. A continuing conduit may be part of a transfer system, for example. The locking of the valve device housing to the catheter hub provides for a reliable tightness of the connection. The design of the valve body may be manifold—provided that it provides a passage for an elongate object, which closes sealingly again after the withdrawal of the object.

In an advantageous embodiment of the invention, the protrusion is a circular cylindrical sleeve with an inwardly directed annular bead behind which radial outer projections of the catheter hub engage in the manner of a ring snap connection. The circular cylindrical sleeve acting as a cylindrical snap element is suitable for connection with conventional catheter hubs that have two diametrically opposed, outwardly directed radial locking cams. The deflection, also referred to as an undercut, occurring during the snapping in, must be dimensioned such that the allowable expansion of the materials employed is not exceeded and that a relaxed, positive engagement is obtained after the snapping in, which cannot be pulled apart in the axial direction. The ring snap connection serves to fix the interconnected elements in a certain relative position. It is an advantage of this connection that it can be mounted with a low joining force. The permanent ring snap connection fixedly retains the outer cone of the housing within the inner cone of the catheter hub, thereby ensuring the tightness of the connection.

The shell of the circular cylindrical sleeve may be closed or may have longitudinal slots forming snap segments. In the first case, the joining force applied upon mounting is larger than in the second case, and increased requirements have to be met by the plastic materials of both components with respect to their elastic deformability. In both cases, it is important that after a short deformation during the joining process, the material restores quickly so that the engagement of locking element and complementary element becomes effective as the contrivance against axial disconnection. With a longitudinal slotting of the circular cylindrical sleeve a quartering or a halving of the circular cylindrical shell is favorable for a permanent snap connection.

The annular bead may approximate a semicircular cross-sectional profile. Alternatively, it may also approximate a trapezoidal cross-sectional profile so that a sliding surface for facilitating the joining process is obtained on the one side, whereas a blocking surface is obtained on the other side. Both cross-sectional profiles are favorable for permanent snap connections.

According to a further advantageous embodiment of the invention, it is provided that the protrusion is formed by at least one sector-shaped cylindrical fin with a groove extending from an opening at the edge to a circumferential portion with a closed end and into which a radial pin at the outer surface of the catheter hub is inserted for engagement in the manner of a bayonet connection.

In this case the disconnection lock is formed by a pin provided at the catheter hub and engaging the groove. The groove that may be open or closed on the outer surface of the sector-shaped cylindrical fin, extends either in L-shape or circumferentially, approximating an S-shape, and in front of its inner end, an engaging projection is formed behind which the pin engages. In both cases, a relative movement of the catheter hub and the valve device housing moves the pin into abutment against the rear end of the groove, where it is engaged so that an axial disconnection lock is obtained.

Preferably, the connection profile at the second end of the housing consists of an inner cone within a pipe socket surrounded on the outside by a thread member. This design is in conformity with a Luer lock, i.e. the connection profile may be connected to a lockable connector having an outer cone so that a conduit may be connected, for example, and a secure connection within a conduit system is provided also at this end of the valve device. Preferably, the valve body is a rubber elastic cup-shaped hollow cylinder that is operated by the outer cone of the connector or a helical spring surrounding the same, as defined in claim 8. As soon as the connector is detached and its outer cone is pulled from the valve device housing, the valve body closes sealingly by the action of the spring and no air can flow into the catheter, neither can body fluid flow therefrom. The valve body passage may be opened again when a guide wire is to be inserted over which the placed catheter may be withdrawn from the vessel and a new catheter without a valve device may be inserted.

BRIEF DESCRIPTION OF THE DRAWINGS

Embodiments of the invention are schematically represented in the drawings.

In the Figures:

FIG. 5 is a side elevational view of a disconnection lock in the form of a bayonet connection, and FIG. 6 is a plan view of the arrangement in the position of FIG. 5.

DESCRIPTION OF THE PREFERRED EMBODIMENTS

Figure 1:
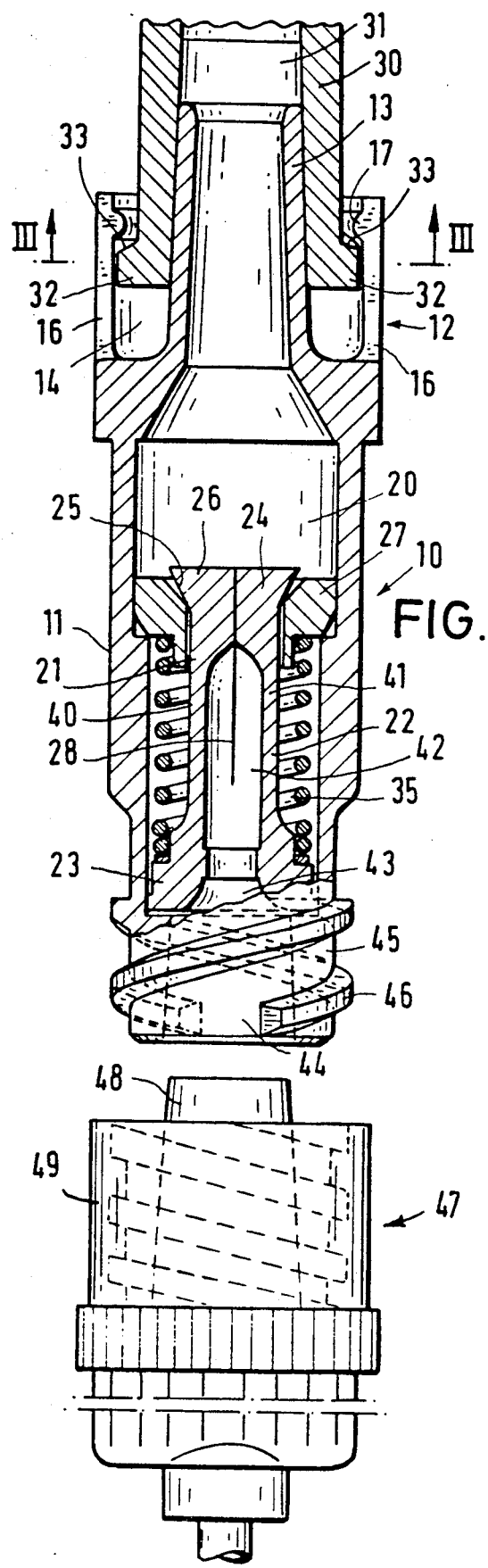
FIG. 1 is a longitudinal section of the valve device with a first embodiment of a ring snap connection.
Figure 2:
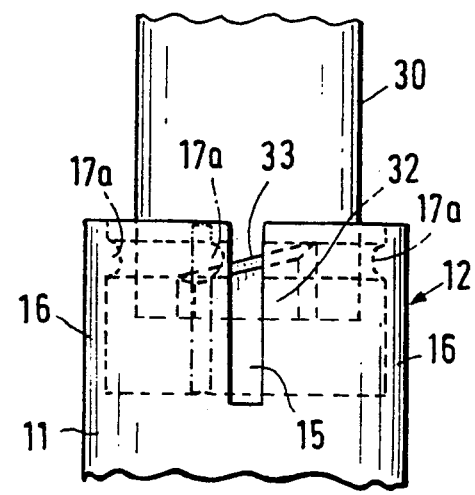
FIG. 2 is a side elevational view for a better understanding of the ring snap connection of FIG. 1.
Figure 3:
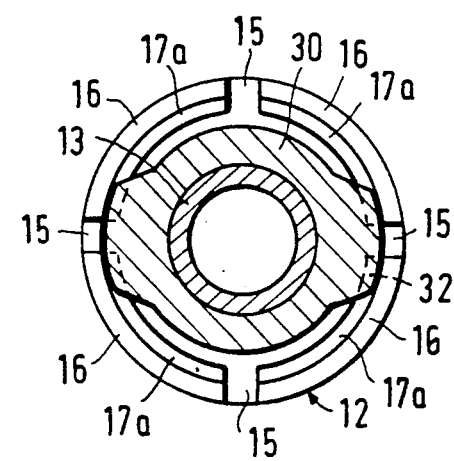
FIG. 3 is a section along line III—III in FIG. 1, with a second embodiment of a ring snap connection.

The valve device 10 of FIGS. 1 to 3 consists of a tubular housing 11 of plastics material formed as an injection moulded part. Moulded to the first end of the housing 11, there is a coaxial circular cylindrical sleeve 12 that surrounds a slightly longer outer cone 13 at a uniform radial distance so that a space 14 is formed between the outer surface of the outer cone 13 and the inner surface of the circular cylindrical sleeve 12. The sleeve 12 and the outer cone 13 are arranged coaxially and lie on the longitudinal axis of the tubular housing 11. In the outer end portion of the sleeve 12, a radially inward directed annular bead 17 is provided that has a semi-circular cross-sectional profile and consists of four equal sectors 17a. The sectors 17a of the annular bead 17 are formed by dividing the circular cylindrical sleeve 12 into four snap segments 16 by four symmetrical longitudinal slots 15. The snap segments 16 form an axial disconnection lock for the catheter hub 30 of a preferably long venous catheter (not illustrated). The catheter hub 30 is also made of plastics material. It has an inner cone 31 into which the outer cone 13 may be set fittingly and sealingly. At the outer edge of the catheter hub 30, two diametrically directed radial outer projections 32 are provided that are designed conventionally as locking cams with an inclined undersurface 33.

Arranged coaxially in the circular cylindrical cavity 20 of the tubular housing 11, there is a rubber elastic cup-shaped hollow cylinder 21 acting as a valve body. The hollow cylinder 21 has a circular cylindrical shaft 22 with a profiled rim 23 at the one end and an axially thick bottom portion 24 at the other end, having a diverging outer annular cone 25 at its free end. Its outer bottom surface 26 is circular and plane. A locking ring 27 having a bevel adapted to the conical form 25 of the bottom portion 24 surrounds the bottom portion 24 in the closed position of the hollow cylinder 21. The thick bottom portion 24 is divided into two legs 40, 41 by a longitudinal slot 28 bisecting the same diametrically and extending far into the shaft 22, the legs being spreadable up to the inner end of the longitudinal slot 28 when released by the locking ring 27. The wall of the hollow cylinder 21 encloses a circular cylindrical longitudinal channel 42 which, on the one hand, ends at the inner base surface of the bottom portion 24, and which, on the other hand, is openly connected with an inner cone 44 of a pipe socket 45 through an opening 43, the pipe socket being surrounded on its outer surface by a thread member 46. A screw-on cap of a connector 47 may be screwed onto the thread portion 46, the outer cone 48 of the connector sealingly projecting into the inner cone 44.

The hollow cylinder 21 is surrounded by a helical spring 35, the one end of which is supported at a shoulder of the outer profile rim 23 of the hollow cylinder 21, while the other end presses against an annular surface of the locking ring 27. The helical spring 35 is biased and retains the hollow cylinder 21 in the closed position in which its bottom portion 24 is drawn into the conical recess of the locking ring 27 and the radial outer portion of the edge of its opening 43 abuts a shoulder at the inner end of the inner cone 44. When the connector is applied at the pipe socket 45, the hollow cylinder 21 is pressed axially into the cavity 20 by the front end face of the outer cone 48, and the two legs 40, 41 are spread apart by the pressure of the inflowing liquid.

When a catheter without a valve has been placed with the help of a guide wire, according to the Seldinger method, and this wire has been withdrawn, the catheter hub 30 and the valve device 10 are assembled. This is done by pushing the sleeve 12 axially onto the catheter hub 30. In doing so, the snap segments 16 are radially deflected by the two radial outer projections 32 and the outer cone 13 penetrates into the inner cone 31. As soon as the outer projections 32 have passed the annular bead 17, the snap segments 16 restore themselves due to the elasticity of the material and the outer projections 32 engage behind the annular bead 17. This ring snap connection forms a disconnection lock that prevents a separation of outer cone 13 and inner cone 31 by axial pulling so that a tight permanent connection between the catheter hub 30 and the valve means 10 is ensured. If the catheter disposed in the vessel is to be replaced, the connector 47 is removed from the pipe socket 45 of the valve means 10 and an operating member is inserted into the inner cone 44 that displaces the hollow cylinder 21 towards the opening direction. A guide wire is put through the hollow cylinder 21 over which the catheter is pulled from the vessel with the valve device 10. A new catheter without a valve is then threaded onto the placed guide wire in the usual way, following the Seldinger method. When the new catheter is in the desired position, a new valve device 10 is connected with its catheter hub 30 in a manner not disconnectable.

Figure 4:
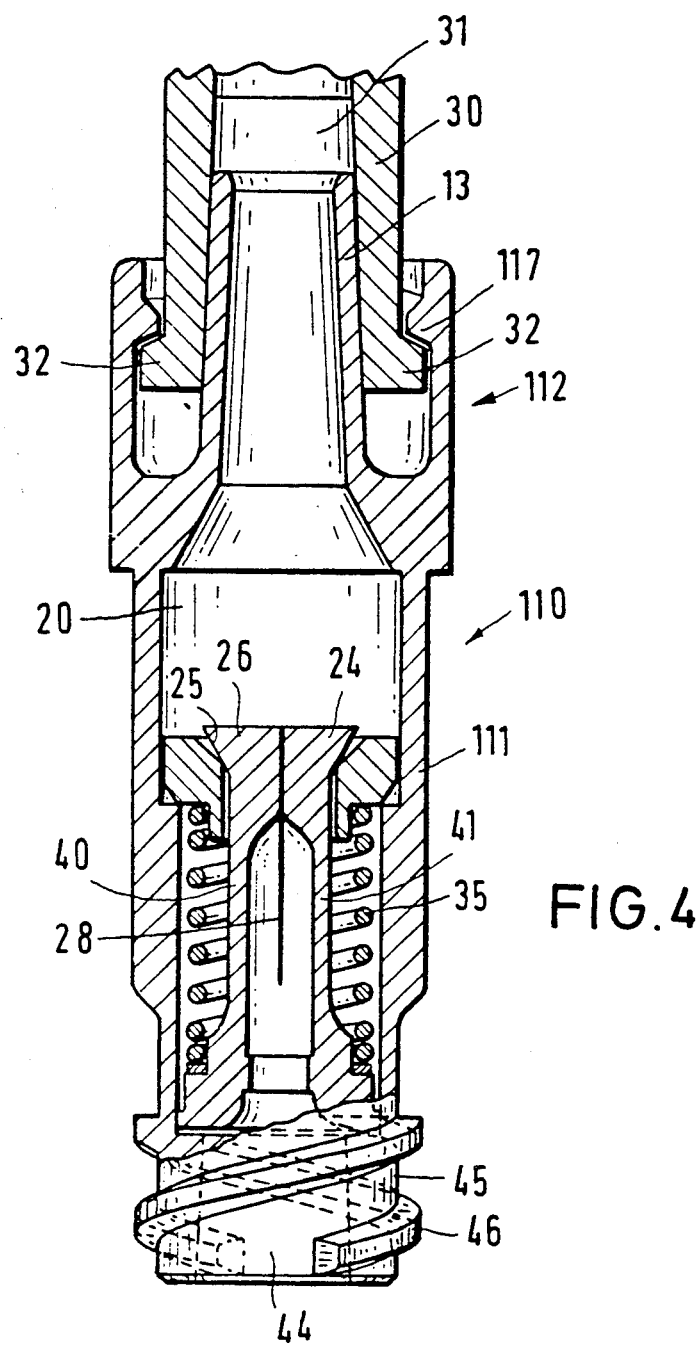

The valve device 110 of FIG. 4 corresponds to the embodiment of FIGS. 1 to 3 as far as the valve body and the connection profile at the second end of the housing 111 are concerned. Only the disconnection lock is of a somewhat different design. In this embodiment, the ring snap connection is formed by a circular cylindrical sleeve 112 with an entirely closed shell. At the outer edge portion of the sleeve 112, an annular bead 117 is provided on the inside at a short distance from the outer edge, the annular bead extending continuously over the entire periphery of the sleeve 112 and having an almost trapezoidal cross-sectional profile. During the joining process, the sleeve 112 is radially expanded and restores itself to the circular cylindrical initial shape as soon as the outer projections 32 of the catheter hub 30 engage behind the annular bead 117 and the snap-in process is ended. Thus, a permanent snap connection is achieved in which the undercut is dimensioned such that the allowable expansion of the plastics material is not exceeded. The bevels of the annular bead 117 are favorable in the joining process. Moreover, they offer the advantage of being well removable from the mould when produced. The snap connection provides for an interconnection without play, if the engagement of the annular bead 117 and the outer projections 32 is effected at such an axial distance from the front end edge of the outer cone 13 that the penetration depth of the outer cone 13 into the inner cone 31 is sufficient to sealingly close the catheter lumen.

In FIGS. 5 and 6, a phantom housing 211 of a valve device is provided with an outer cone 213 projecting coaxially from the front end of the housing 211. A sector-shaped cylindrical fin 50 that is provided on the housing 211 with a radial distance from the outer cone 213, serves as a disconnection lock. A groove 51 is formed in the fin 50, which perforates the fin 50 in the manner of a slot. The groove 51 is open at 52 at one longitudinal edge of the fin and extends with a circumferential pitch in a slight S-shaped curve up to its closed end 53 that forms an upward directed pocket. In the groove 51, an engaging projection 55 is arranged at the beginning of the pocket, by which the passage of the groove is narrowed. The fin 50 is shorter in the axial direction than the outer cone 213. Upon assembling the inner cone 31 and the outer cone 213, a radial pin 54 is moved into the groove 54 by turning, the pin radially projecting from the outer surface of the catheter hub 30. The pin 54 penetrating into the groove 51 and the fin 50 together form a kind of bayonet connection, wherein, in the locked position, the pin 54 engages behind the engaging projection 55 so that it is trapped in the pocket at the closed end 53 of the groove 51. In this state, locked against disconnection, the outer cone 213 is firmly drawn into the inner cone 31 so that the connection is tight. Movements of the conduit line into which the valve device is installed cannot loosen the connection and its firmness upon the action of axial forces is ensured. Movements of the conduit line between a transfer system and a patient occur in particular during the increasingly practiced early mobilisation of patients that carry the transfer system along when moving about freely.

We claim:

1. A valve device configured for attachment to a catheter having a catheter hub defining an inner cone and a locking element, the valve device comprising
   a substantially tubular housing defining an axis, a first end and a second end,
   an outer cone provided at the first end of the housing, the outer cone defining a first end and a second end and being configured to fit the inner cone of the catheter hub,
   a valve body disposed within the housing,
   a substantially axial protrusion provided on the housing, the substantially axial protrusion and the outer cone mutually defining a radial space configured for receiving the locking element of the catheter hub, the substantially axial protrusion comprising a locking element, the locking element of the axial protrusion being arranged between the first end and the second end of the outer cone, the outer cone being configured to exert a radially outwardly directed pressing force on the locking element of the catheter hub when the locking element of the catheter hub is received in the radial space, the locking element of the axial protrusion being configured to define a radially symmetric cross section and to engage the locking element of the catheter hub when the locking element of the catheter hub is received in the radial space and to prevent removal of the locking element of the catheter hub in a direction substantially parallel to the axis of the housing when the locking element of the catheter hub is received in the radial space, whereby the locking element of the axial protrusion and the locking element of the catheter hub mutually form a substantially inseparable connection lock when the locking element of the catheter hub is received in the radial space.

2. The device of claim 1, wherein the second end of the housing defines a connection profile configured for connecting the housing and a connector.

3. A valve device configured for attachment to a catheter having a catheter hub defining an inner cone and a locking element, the locking element comprising at least one outwardly directed radial projection associated with the catheter hub, the valve device comprising:

a substantially tubular housing defining an axis, a first end and a second end, an outer cone provided at the first end of the housing, the outer cone being configured to fit the inner cone of the catheter hub, a valve body disposed within the housing, a substantially axial protrusion provided on the housing, the substantially axial protrusion and the outer cone mutually defining a radial space configured for receiving the locking element of the catheter hub, the substantially axial protrusion comprising a locking element, the locking element of the axial protrusion being arranged between the first end and the second end of the outer cone, the outer cone being configured to exert a radially outwardly directed pressing force on the locking element of the catheter hub when the locking element of the catheter hub is received in the radial space, the locking element of the axial protrusion being configured to engage the locking element of the catheter hub when the locking element of the catheter hub is received in the radial space and to prevent removal of the locking element of the catheter hub in a direction substantially parallel to the axis of the housing when the locking element of the catheter hub is received in the radial space, whereby the locking element of the axial protrusion and the locking element of the catheter hub mutually form a substantially inseparable connection lock when the locking element of the catheter hub is received in the radial space, wherein the axial protrusion comprises a substantially circular cylindrical sleeve and the locking element of the axial protrusion comprises an inwardly directed annular bead, and wherein the inwardly directed annular bead and the at least one outwardly directed radial projection are mutually engagable to thereby form a ring snap connection.

4. The device of claim 3, wherein the substantially circular cylindrical sleeve defines a closed shell.

5. The device of claim 3, wherein the substantially circular cylindrical sleeve defines a plurality of substantially longitudinal slots dividing the sleeve into a plurality of snap segments.

6. A valve device configured for attachment to a catheter having a catheter hub defining an inner cone and a locking element, the valve device comprising a substantially tubular housing defining an axis, a first end and a second end, an outer cone provided at the first end of the housing, the outer cone being configured to fit the inner cone of the catheter hub, a valve body disposed within the housing, a substantially axial protrusion provided on the housing, the substantially axial protrusion and the outer cone mutually defining a radial space configured to receive the locking element of the catheter hub, the substantially axial protrusion comprising a locking element, the locking element of the axial protrusion being configured to engage the locking element of the catheter hub when the locking element of the catheter hub is received in the radial space, whereby the locking element of the axial protrusion and the locking element of the catheter hub mutually form a disconnection lock when the locking element of the catheter hub is received in the radial space, wherein the axial protrusion comprises a substantially circular cylindrical sleeve and the locking element of the axial protrusion comprises an inwardly directed annular bead, the locking element of the catheter hub comprises at least one outwardly directed radial projection associated with the catheter hub, and wherein the inwardly directed annular bead and the at least one outwardly directed radial projection are mutually engagable to thereby form a ring snap connection, and wherein the annular bead defines a substantially semi-circular cross section.

7. A valve device configured for attachment to a catheter having a catheter hub defining an inner cone and a locking element, the valve device comprising:

a substantially tubular housing defining an axis, a first end and a second end, an outer cone provided at the first end of the housing, the outer cone being configured to fit the inner cone of the catheter hub, a valve body disposed within the housing, a substantially axial protrusion provided on the housing, the substantially axial protrusion and the outer cone mutually defining a radial space configured to receive the locking element of the catheter hub, the substantially axial protrusion comprising a locking element, the locking element of the axial protrusion being configured to engage the locking element of the catheter hub when the locking element of the catheter hub is received in the radial space, whereby the locking element of the axial protrusion and the locking element of the catheter hub mutually form a disconnection lock when the locking element of the catheter hub is received in the radial space, wherein the axial protrusion comprises a substantially circular cylindrical sleeve and the locking element of the axial protrusion comprises an inwardly directed annular bead, the locking element of the catheter hub comprises at least one outwardly directed radial projection associated with the catheter hub, and wherein the inwardly directed annular bead and the at least one outwardly directed radial projection are mutually engagable to thereby form a ring snap connection, and wherein the annular bead defines a substantially trapezoidal cross section.

8. A valve device configured for attachment to a catheter having a catheter hub defining an inner cone and a locking element, the valve device comprising:

a substantially tubular housing defining an axis, a first end and a second end, an outer cone provided at the first end of the housing, the outer cone defining a first end and a second end and being configured to fit the inner cone of the catheter hub, a valve body disposed within the housing, a substantially axial protrusion provided on the housing, the substantially axial protrusion and the outer cone mutually defining a radial space configured for receiving the locking element of the catheter hub, the substantially axial protrusion comprising a locking element, the locking element of the axial protrusion being arranged between the first end and the second end of the outer cone, the outer cone being configured to exert a radially outwardly directed pressing force on the locking element of the catheter hub when the locking element of the catheter hub is received in the radial space, the locking element of the axial protrusion being configured to engage the locking element of the catheter hub when the locking element of the catheter hub is received in the radial space and to prevent removal of the locking element of the catheter hub in a direction substantially parallel to the axis of the housing when the locking element of the catheter hub is received in the radial space, whereby the locking element of the axial protrusion and the locking element of the catheter hub mutually form a substantially inseparable connection lock when the locking element of the catheter hub is received in the radial space, wherein the locking element of the axial protrusion comprises at least one substantially sector-shaped cylindrical fin defining an edge and having a groove therein, the groove extending substantially circumferentially from an opening at the edge of the fin, the locking element of the catheter hub comprises a substantially radial pin disposed on an outer surface of the catheter hub, and wherein the groove and the radial pin are configured for mutual locking engagement.

9. A valve device configured for attachment to a catheter having a catheter hub defining an inner cone and a locking element, the valve device comprising:

a substantially tubular housing defining an axis, a first end and a second end, an outer cone provided at the first end of the housing, the outer cone being configured to fit the inner cone of the catheter hub, a valve body disposed within the housing, a substantially axial protrusion provided on the housing, the substantially axial protrusion and the outer cone mutually defining a radial space configured to receive the locking element of the catheter hub, the substantially axial protrusion comprising a locking element, the locking element of the axial protrusion being configured to engage the locking element of the catheter hub when the locking element of the catheter hub is received in the radial space, whereby the locking element of the axial protrusion and the locking element of the catheter hub mutually form a disconnection lock when the locking element of the catheter hub is received in the radial space, wherein the second end of the housing defines a connection profile configured for connecting the housing and a connector and wherein the connection profile comprises a pipe socket defining an exterior and an interior, the exterior of the pipe socket comprising a thread member, the interior of the pipe socket comprising an inner cone, the inner cone defining a cross section and an inner end having a shoulder, and wherein the second end of the housing defines a cavity, and further comprising:

a locking ring fixed within the housing and having a central opening, a flexible, cup-shaped hollow cylinder including a bottom portion having an axial slot defining at least two legs, the cylinder being arranged for axial displacement within the cavity, the cylinder comprising an opening edge having a radially outer portion and a radially inner portion, a spring for biasing the cylinder in a closed position wherein the radially outer portion of the cylinder is pressed against the shoulder at the inner end of the inner cone and the radially inner portion of the cylinder projects into the cross section of the inner cone, and the locking ring and the cylinder being disposed so that the bottom portion of the cylinder is advanceable through the central opening of the locking ring against the biasing action of the spring, whereby the at least two legs defined by the slot are released.

* * * * *